US008715987B2

(12) United States Patent
Johnson et al.

(10) Patent No.: US 8,715,987 B2
(45) Date of Patent: May 6, 2014

(54) SOLUBILIZED PHOSPHOLIPIDS FOR STABILIZING NUCLEIC ACID POLYMERASES

(75) Inventors: Donald Johnson, Brookline, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/450,549

(22) Filed: Apr. 19, 2012

(65) Prior Publication Data
US 2012/0282669 A1 Nov. 8, 2012

Related U.S. Application Data

(60) Provisional application No. 61/481,437, filed on May 2, 2011, provisional application No. 61/494,458, filed on Jun. 8, 2011.

(51) Int. Cl.
*C12N 9/96* (2006.01)
(52) U.S. Cl.
USPC .......................................................... 435/188
(58) Field of Classification Search
None
See application file for complete search history.

(56) References Cited

U.S. PATENT DOCUMENTS

| | | | |
|---|---|---|---|
| 4,889,818 | A | 12/1989 | Gelfand et al. |
| 5,047,342 | A | 9/1991 | Chatterjee |
| 5,079,352 | A | 1/1992 | Gelfand et al. |
| 5,270,179 | A | 12/1993 | Chatterjee |
| 5,374,553 | A | 12/1994 | Gelfand et al. |
| 5,436,149 | A | 7/1995 | Barnes |
| 5,512,462 | A | 4/1996 | Cheng |
| 5,614,365 | A | 3/1997 | Tabor et al. |
| 5,792,612 | A | 8/1998 | Kinnunen et al. |
| 6,127,155 | A | 10/2000 | Gelfand et al. |
| 6,242,235 | B1 | 6/2001 | Shultz et al. |
| 6,881,559 | B2 | 4/2005 | Sobek et al. |
| 7,429,468 | B2 | 9/2008 | Sobek et al. |
| 7,541,170 | B2 | 6/2009 | Wang et al. |
| 7,666,645 | B2 | 2/2010 | Wang |
| 7,846,703 | B2 | 12/2010 | Kobayashi et al. |
| 2004/0091873 | A1 | 5/2004 | Sorge et al. |
| 2005/0048530 | A1 | 3/2005 | Borns |
| 2007/0141591 | A1 | 6/2007 | Borns |
| 2008/0064071 | A1 | 3/2008 | Hogrefe et al. |
| 2010/0099150 | A1 | 4/2010 | Fang et al. |
| 2010/0159528 | A1 | 6/2010 | Liu et al. |

FOREIGN PATENT DOCUMENTS

| | | | |
|---|---|---|---|
| CN | 101570792 | A * | 11/2009 |
| WO | WO9206188 | A2 | 4/1992 |
| WO | WO9206200 | A1 | 4/1992 |
| WO | WO9610640 | A1 | 4/1996 |
| WO | WO0132887 | A1 | 5/2001 |
| WO | WO2008013885 | A2 | 1/2008 |
| WO | WO2008077017 | A2 | 6/2008 |

OTHER PUBLICATIONS

Manual Translation CN 101570792A, Nov. 2009.*
Barnes, WM, "The fidelity of Taq polymerase catalyzing PCR is improved by an N-terminal deletion.", Gene, 112(1):29-35, 1992.
Cann, et al., "A heterodimeric DNA polymerase: evidence that members of Euryarchaeota possess a distinct DNA polymerase.", Proc. Natl. Acad. Sci. USA, 95:14250-5, 1998.
Capitani,et al, "Effect of phosphatidylcholine vesicles on the activity of DNA polymerase-α.", Mol and Cell Biochem 27:137-138,1979.
Chien, et al, "Deoxyribonucleic acid polymerase from the extreme thermophile *Thermus aquaticus*.",Journal of Bacteriology, 127:1550, 1976.
Diaz, et al, "Accuracy of replication in the polymerase chain reaction. Comparison between *Thermotoga maritima* DNA polymerase and *Thermus aquaticus* DNA polymerase.", Brazilian Journal of Medical and Biological Research, 31:1239, 1998.
Eckert , et al, "The Fidelity of DNA Polymerases used in the polymerase chain reactions", Oxford University Press, New York, NY, pp. 225-244, 1991.
Flaman, et al, "A Rapid PCR Fidelity Assay.", Nucleic Acids Research, 22(15):3259-3260,1994.
Gill, et al. "Nucleic acid isothermal amplification technologies.", Nucleosides, Nucleotides and Nucleic Acids 27(3): 224-43, 2008.
Hinnisdaels, et al, "Direct Cloning of PCR Products Amplified with Pwo DNA Polymerase.", Biotechniques 20:186-8, 1996.
Kim, et al, "Isothermal DNA amplification in bioanalysis: strategies and applications.", Bioanalysis 3(2): 227-39, 2011.
Kornberg, et al., "DNA Replication.", 2nd edition, W. H. Freeman, NewYork, N.Y., pp. 101-115, 150-152, 157, 165, 169-173, 192-193, 223-225, 1992.
Lawyer, et al, "High-level expression, purification, and enzymatic characterization of full-length Thermus aquaticus DNA polymerase and a truncated form deficient in 5' to 3' exonuclease activity.", PCR Meth. Appl., 2:275-287,1993.
Lecomte, et al, "Selective inactivation of the 3' to 5' exonuclease activity of *Escherichia coli* DNA polymerase I by heat.", Nucleic Acids Res., 11:7505, 1983.
Lundberg, et al, "High-fidelity amplification using a thermostable DNA polymerase isolated from *Pyrococcus furiosus*.", Gene 108(1):1-6, 1991.
MacDonald, et al, "Small-volume extrusion apparatus for preparation of large, unilamellar vesicles.",Biochim. Biophys. Acta 1061:297-303, 1991.
Myers, et al, "Reverse transcription and DNA amplification by a *Thermus thermophilus* DNA polymerase.", Biochemistry, 30:7661-7666, 1991.
Nordstrom, et al., "Characterization of bacteriophage T7 DNA polymerase purified to homogeneity by antithioredoxin immunoadsorbent chromatography", Journal of Biological Chemistry, 256:3112, 1981.

(Continued)

*Primary Examiner* — Suzanne M Noakes
(74) *Attorney, Agent, or Firm* — New England Biolabs, Inc; Harriet M. Strimpel

(57) ABSTRACT

Compositions and methods are provided that relate to solubilized phospholipids and their use in stabilizing nucleic acid polymerases. For example, a phospholipid with a tail containing at least 8 carbons can be solubilized in the presence of an amphipathic molecule.

10 Claims, 14 Drawing Sheets

(56) References Cited

OTHER PUBLICATIONS

Stenesh, et al, "DNA polymerase from mesophilic and thermophilic bacteria. III. Lack of fidelity in the replication of synthetic polydeoxyribonucleotides by DNA polymerase from *Bacillus licheniformis* and *Bacillus stearothermophilus*.", Biochimica et Biophysica Acta, 475:32, 1977.

Takagi, et al, "Characterization of DNA polymerase from *Pyrococcus* sp. strain KOD1 and its application to PCR.", Applied and Environmental Microbiology, 63:4504, 1997.

* cited by examiner

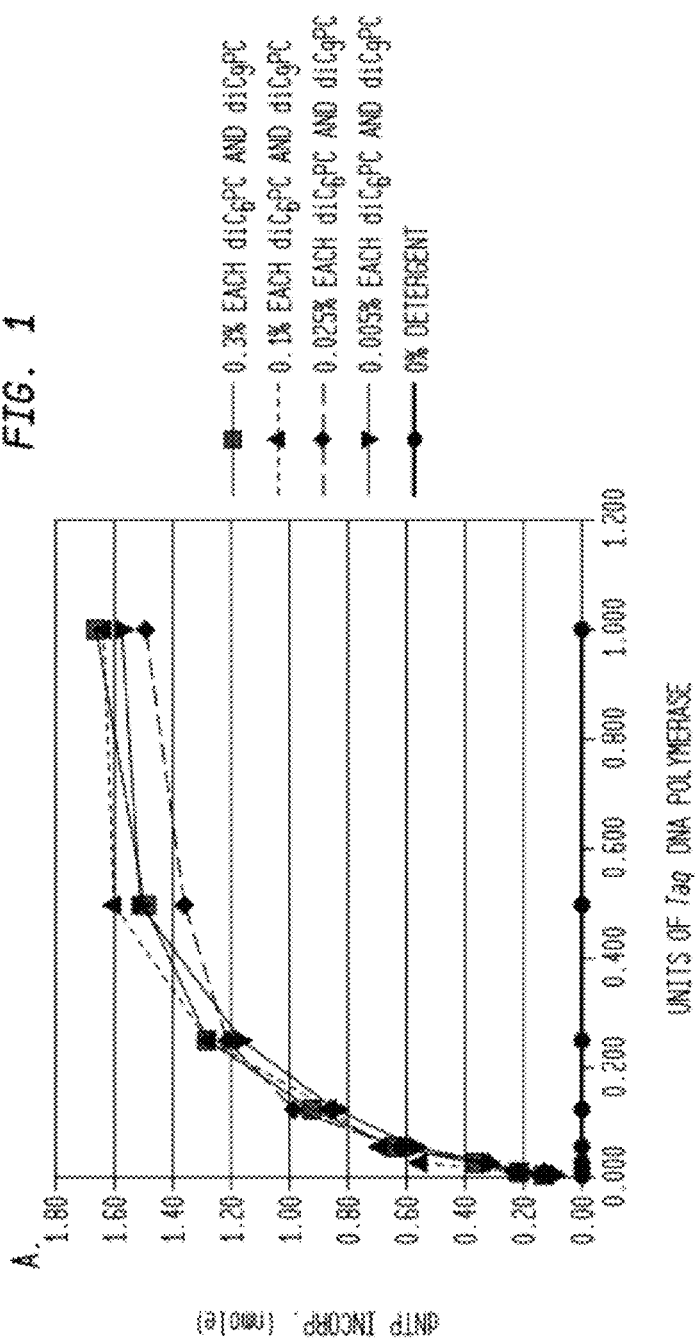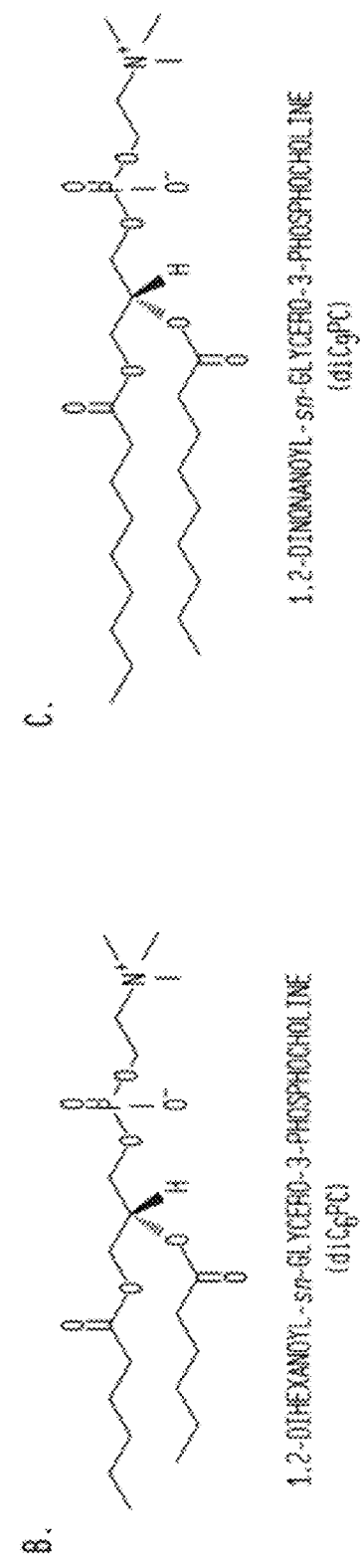

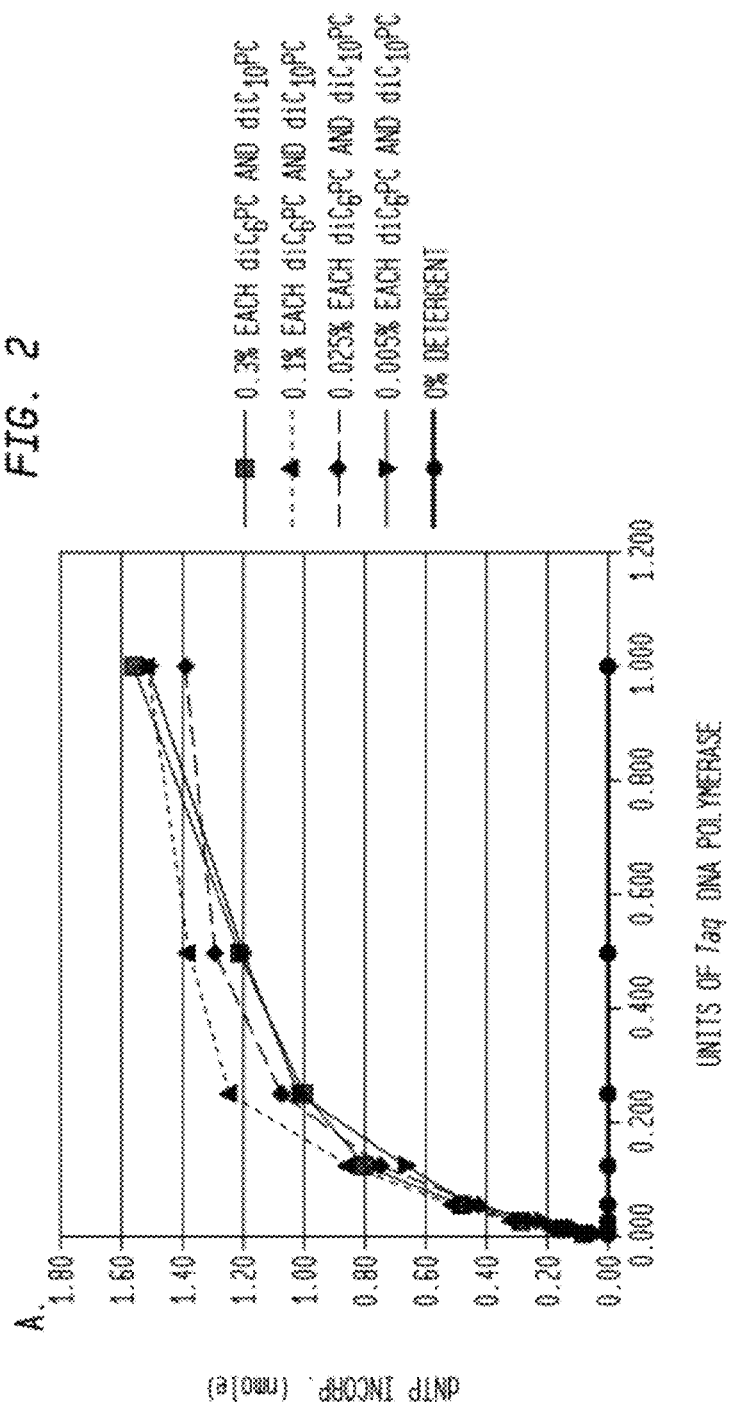
FIG. 2
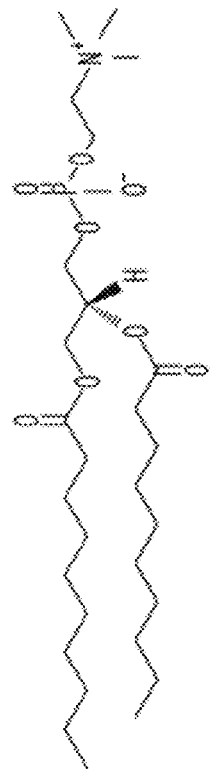
B. 1,2-DIHEXANOYL-sn-GLYCERO-3-PHOSPHOCHOLINE (diC6PC)
C. 1,2-DIDECANOYL-sn-GLYCERO-3-PHOSPHOCHOLINE (diC10PC)

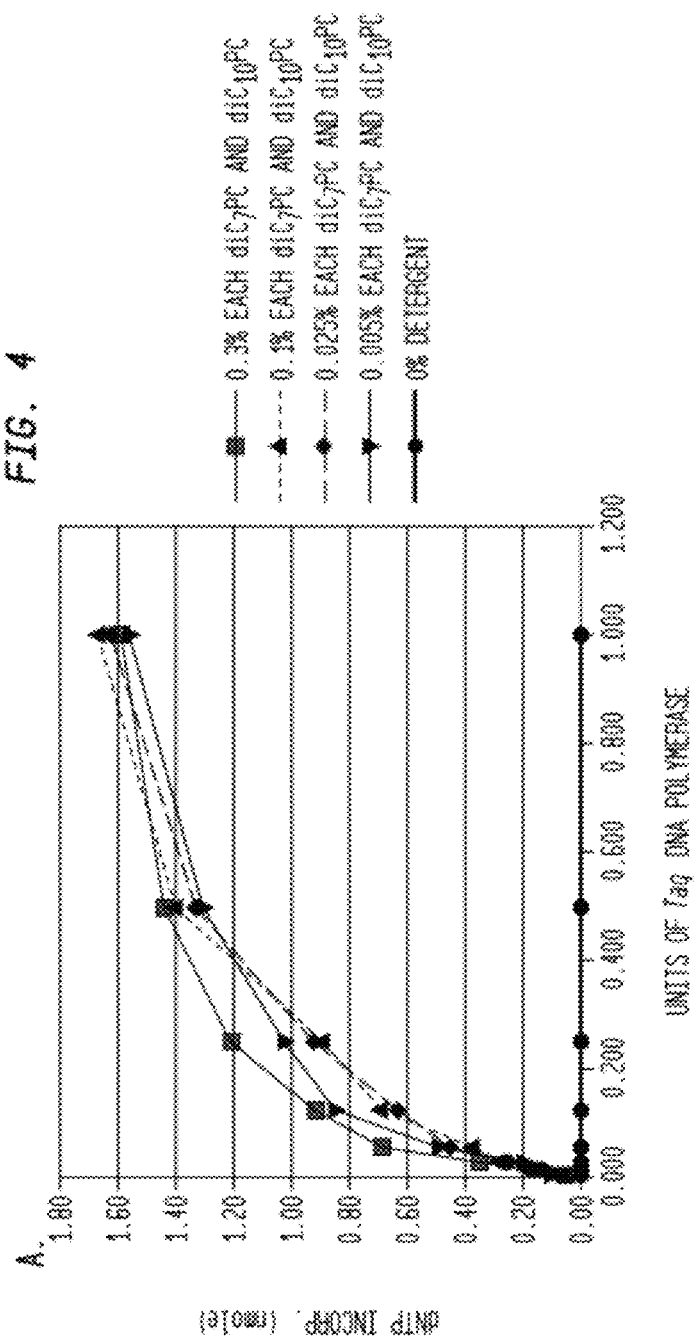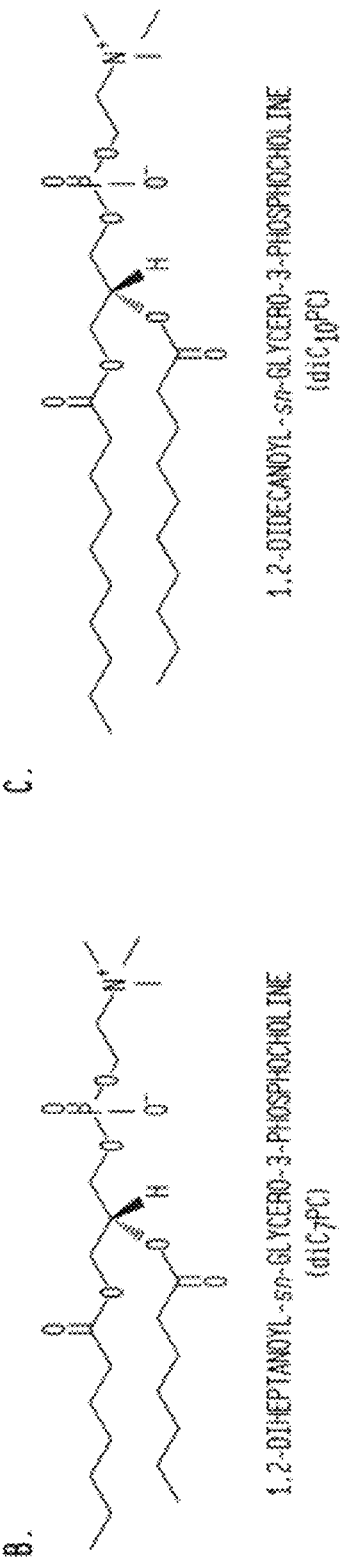
FIG. 4

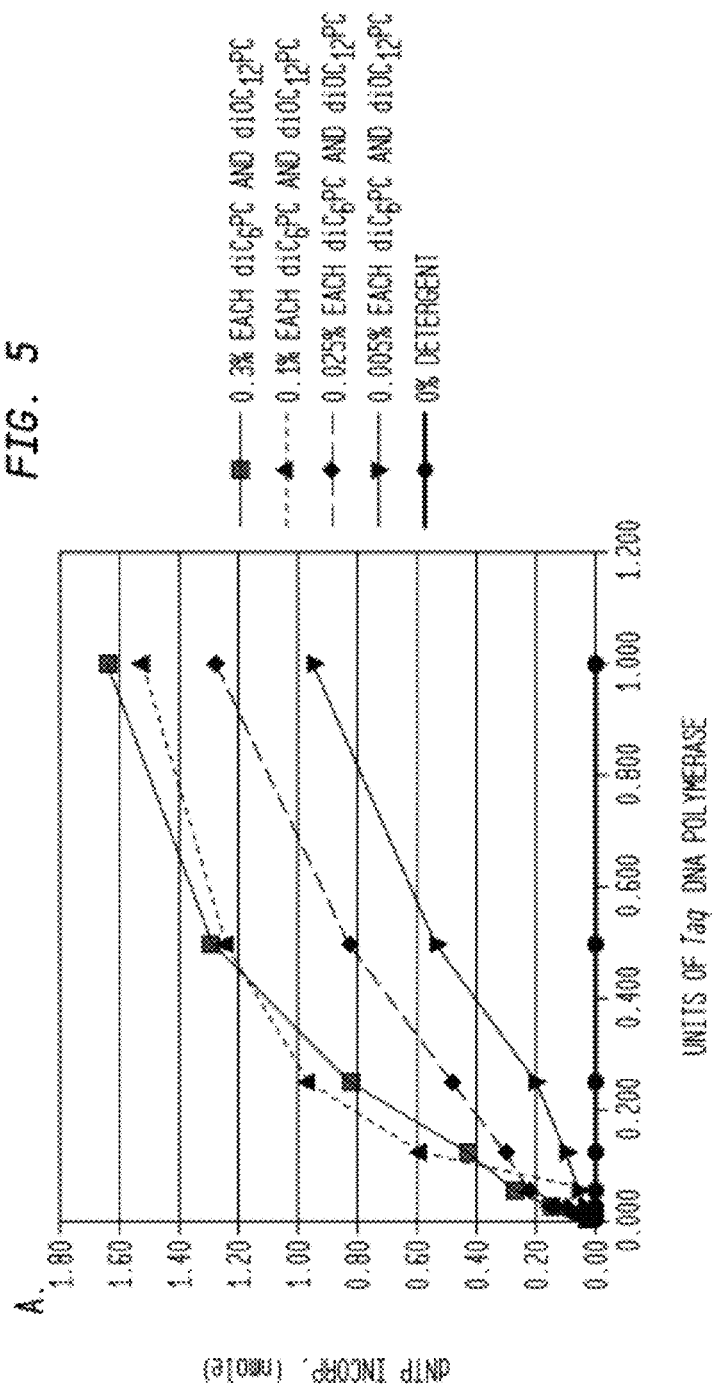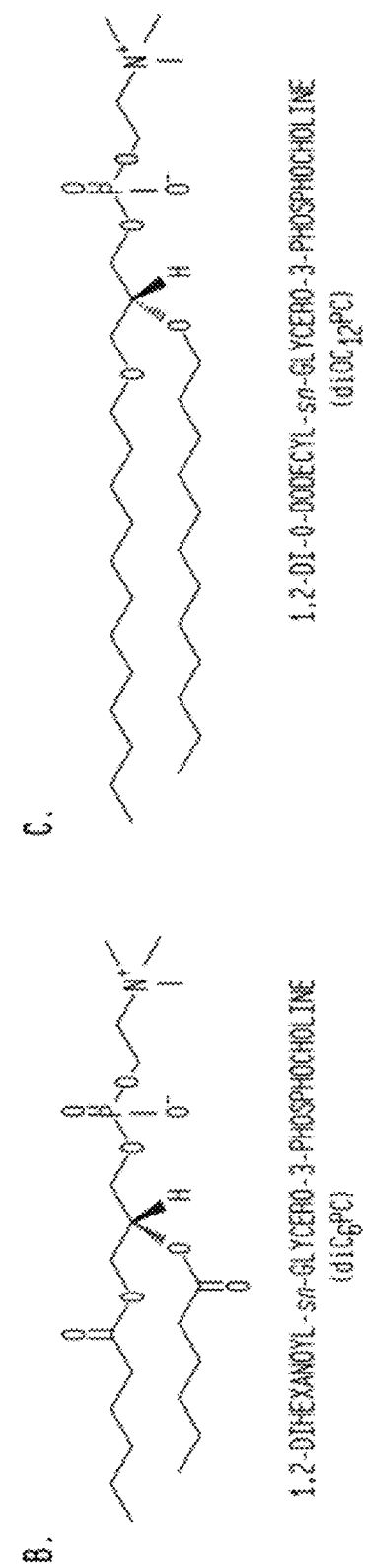
FIG. 5

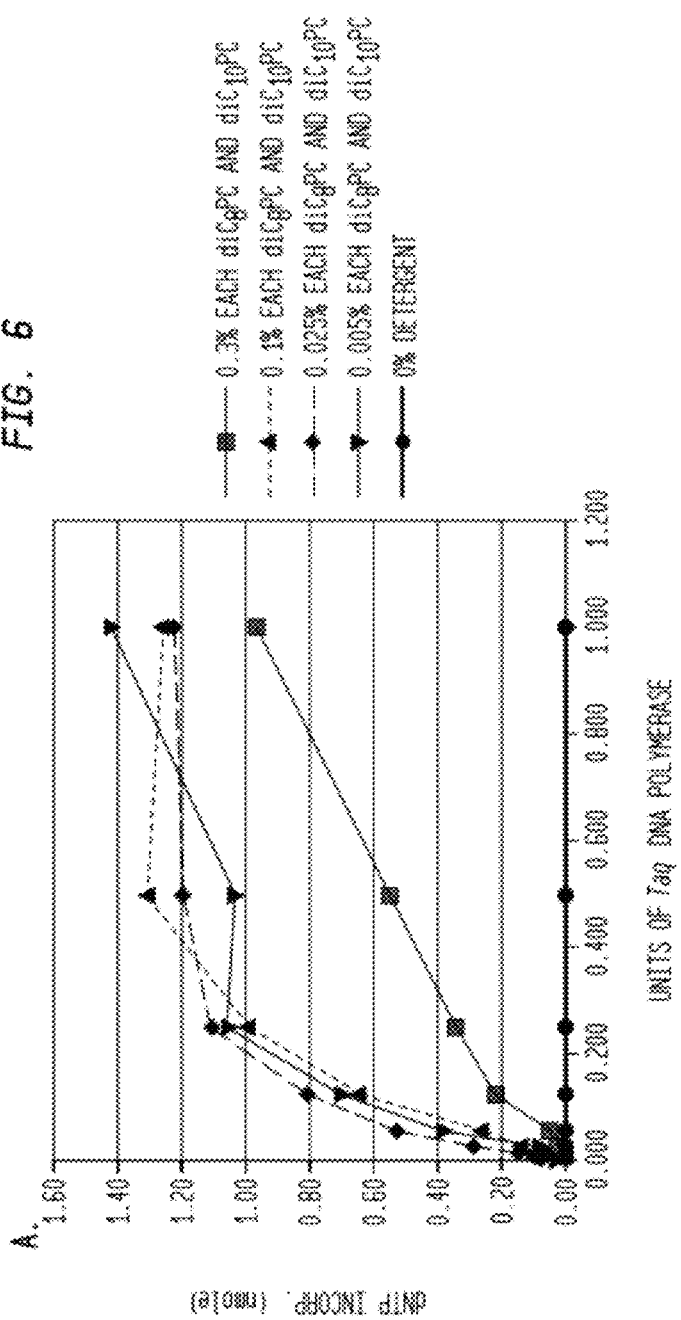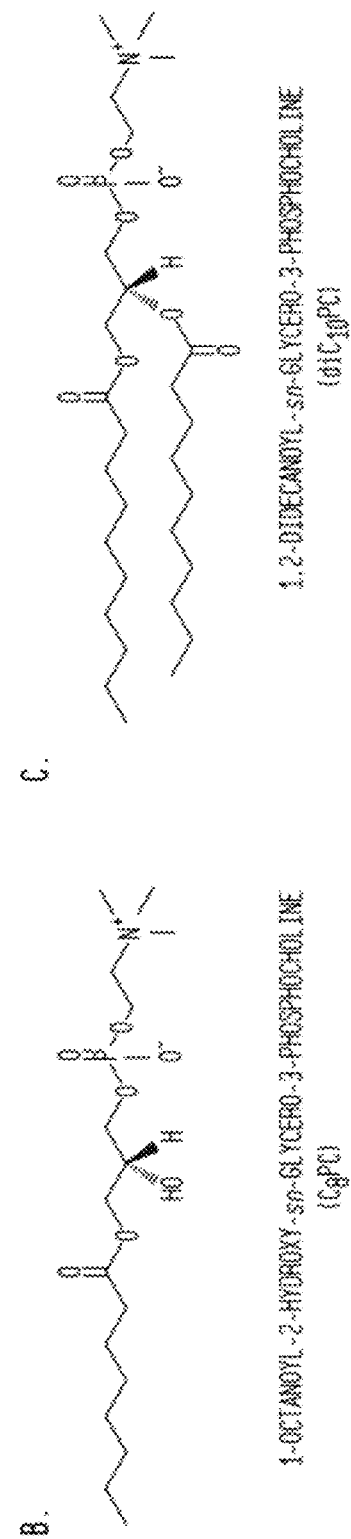
FIG. 6

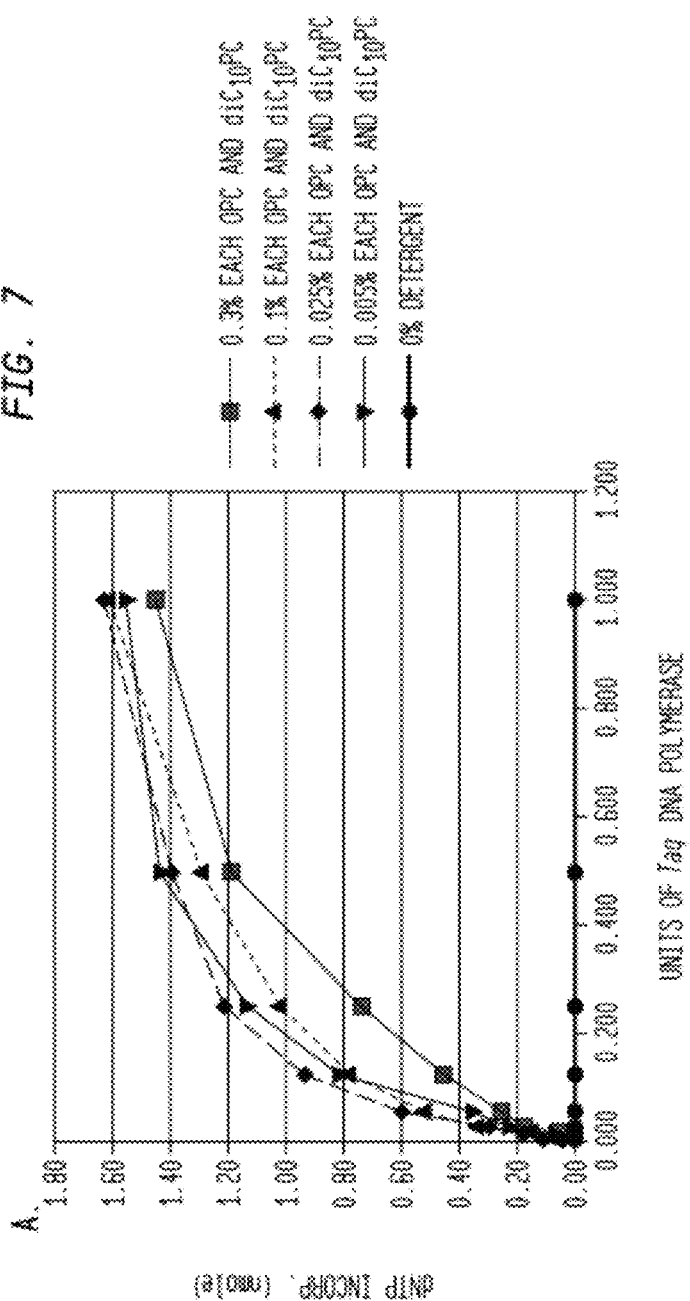
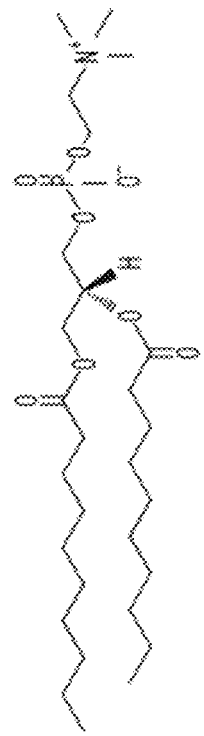
FIG. 7

FIG. 8
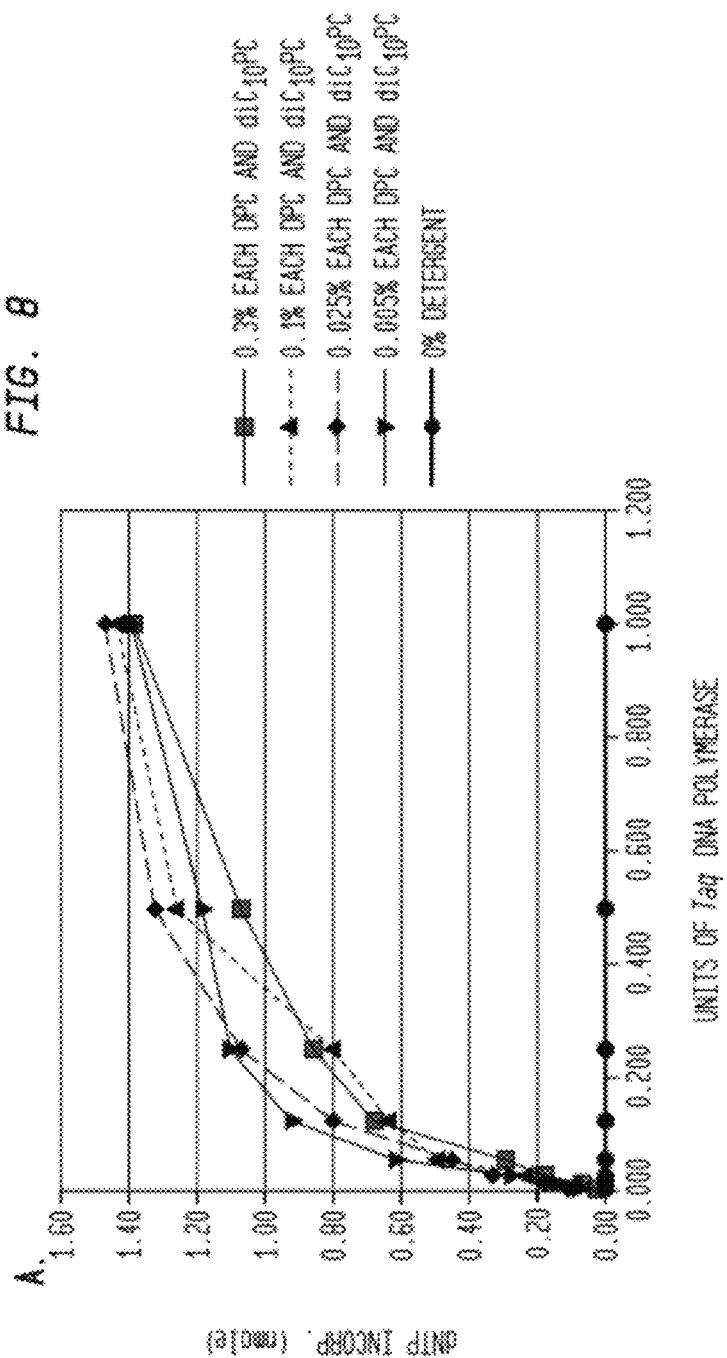
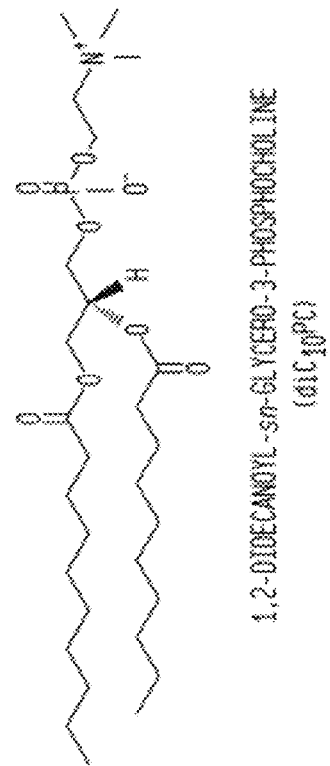
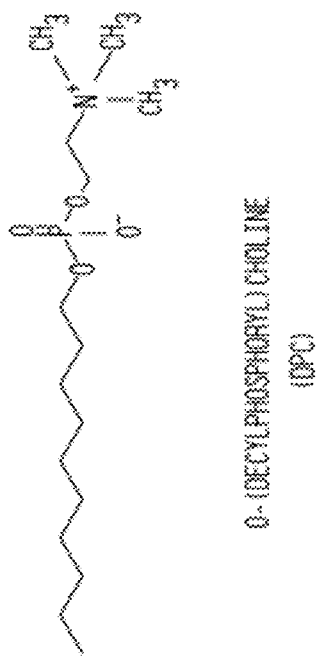

FOR STABILIZERS: n≥8, SOLUBILIZERS: n<8

A.
PHOSPHOLIPIDS CORE

B.
$R_1$ AND $R_2$ COULD BE ANY OF THE FOLLOWING:

$-C_nH_{2n+1}$
$-C_nH_{2n-1}$
$-C_nH_{2n-3}$
$-C_nH_{2n-5}$
$-C_nH_{2n-7}$
$-C_nH_{2n-9}$

C.
$R_3$ COULD BE ANY OF THE FOLLOWING:

$-C_5H_{13}N$
$-H$
$-C_2H_7N$
$-C_3H_7O_2$
$-C_3H_6O_2$
$-C_6H_{11}O_5$

FOR STABILIZERS: n≥4

A.
TRIGLYCERIDES CORE

B.
$R_1, R_2$ AND $R_3$ COULD BE ANY OF THE FOLLOWING:

$-C_nH_{2n+1}$
$-C_nH_{2n-1}$
$-C_nH_{2n-3}$
$-C_nH_{2n-5}$
$-C_nH_{2n-7}$
$-C_nH_{2n-9}$

FOR STABILIZERS: n≥8, SOLUBILIZERS: n≤8

A.
ETHER LIPIDS CORE

B.
$R_1$ AND $R_2$ COULD BE ANY OF THE FOLLOWING:

$-C_nH_{2n+1}$
$-C_nH_{2n-1}$
$-C_nH_{2n-3}$
$-C_nH_{2n-5}$
$-C_nH_{2n-7}$
$-C_nH_{2n-9}$

C.
$R_3$ COULD BE ANY OF THE FOLLOWING:

$-C_5H_{13}N$
$-H$
$-C_2H_7N$
$-C_3H_7O_2$
$-C_3H_6O_2$
$-C_6H_{11}O_5$

FOR STABILIZERS: n=8, SOLUBILIZERS: n=8

A. SPHINGOLIPIDS CORE

B. $R_1$ AND $R_2$ COULD BE ANY OF THE FOLLOWING:

- $-C_nH_{2n+1}$
- $-C_nH_{2n-1}$
- $-C_nH_{2n-3}$
- $-C_nH_{2n-5}$
- $-C_nH_{2n-7}$
- $-C_nH_{2n-9}$

C. $R_3$ COULD BE ANY OF THE FOLLOWING:

- $-PO_3C_5H_{13}N$
- $-H$
- $-PO_3C_2H_7N$
- $-PO_3C_3H_7O_2$
- $-PO_3C_3H_6O_2$
- $-PO_3C_6H_{11}O_5$
- $-P_nO_{3n}H$
- $-C_{6n}H_{10n+1}O_{5n}$
- $-C_{6n}H_{10n}O_{5n}$
- $-C_{6n}H_{10n-1}O_{5n}$
- $-C_{6n}H_{10n-2}O_{5n}$
- $-C_{6n}H_{10n-3}O_{5n}$
- $-C_{6n}H_{10n+7n}O_{5n+3n}N_n$

FOR STABILIZERS: n≥8, SOLUBILIZERS: n≤8

A.
PLASMINOGEN CORE

B.
$R_1$ AND $R_2$ COULD BE ANY OF THE FOLLOWING:

$-C_nH_{2n+1}$
$-C_nH_{2n-1}$
$-C_nH_{2n-3}$
$-C_nH_{2n-5}$
$-C_nH_{2n-7}$
$-C_nH_{2n-9}$

C.
$R_3$ COULD BE ANY OF THE FOLLOWING:

$-C_5H_{13}N$
$-H$
$-C_2H_7N$
$-C_3H_7O_2$
$-C_3H_6O_2$
$-C_6H_{11}O_5$

SEQUENCE LISTING

<160> NUMBER OF SEQ ID NOS: 1

<210> SEQ ID NO 1
<211> LENGTH: 24
<212> TYPE: DNA
<213> ORGANISM: artificial sequence
<220> FEATURE:
<223> OTHER INFORMATION: primer

<400> SEQUENCE: 1
cgccagggtt ttcccagtca cgac					24

SOLUBILIZED PHOSPHOLIPIDS FOR STABILIZING NUCLEIC ACID POLYMERASES

CROSS REFERENCE

This application claims priority from U.S. Provisional Application No. 61/481,437 filed May 2, 2011, herein incorporated by reference, and U.S. Provisional Application No. 61/494,458 filed Jun. 8, 2011.

BACKGROUND

Polymerases may have suboptimal activity associated with their stability under reaction conditions. See for example, Eckert and Kunkel, "The Fidelity of DNA Polymerase and the Polymerases used in the PCR" in *Polymerase Chain Reaction I: A Practical Approach*, McPherson, et al., eds., Oxford University Press, New York, N.Y., (1991), pp. 235-244.

Early work reported by Capitani, et al., (*Molecular and Cellular Biochemistry*, 27:137-138 (1979)) described the use of phosphatidylcholine in the form of vesicles to stimulate the activity of DNA polymerase-α. U.S. Pat. No. 5,792,612 reported the use of phospholipids in a suspension or matrix in the form of unilamellar liposomes which are combined with polymerases and DNA or RNA to increase the efficiency of polymerase-dependent amplification reactions. The unilamellar liposomes were prepared by extrusion through 0.1 µM polycarbonate membranes with a LiposoFast matrix homogenizer as reported by MacDonald, et al., (*Biochimica et Biophysica Acta-Biomembranes*, 1061:297-303 (1991)) and were added prior to initiation of the reaction.

One of the limitations of using long-chain phosphatidylcholine phospholipids relates to their insolubility, which necessitates the use of an extruder to create pre-formed vesicles or liposomes. Another related limitation is that vesicles and liposomes have adverse effects on certain physical attributes such as light scattering in activity assays.

Polymerases for use in polymerase-dependent amplification have reportedly benefited from the stabilizing effect of non-phospholipid detergents characterized by 3-[(3-Cholamidopropyl) dimethylammonio]-1-propanesulfonate (CHAPS) (U.S. Pat. Nos. 6,881,559 and 7,429,468). Later-filed applications claim CHAPS under the broader description of zwitterionic detergents for use in DNA amplification (International Publication Nos. WO 2008/013885; WO 2008/077017; U.S. Publication No. 2010/0099150).

Other agents used for polymerase stabilization have also been described. U.S. Pat. No. 6,242,235 describes the use of polyethoxylated surfactants with polymerases and International Publication No. WO 2008/013885 similarly describes a polymerase with a surfactant which "has a relatively small hydrophobic head and two long hydrophilic ethylene oxide tails that do not form micelles." The use of non-ionic polymeric detergents and anionic detergents are described in U.S. Pat. Nos. 6,127,155 and 7,846,703 and U.S. Publication Nos. 2010/0159528

There is a continuing need to refine and improve stabilizers for polymerases so as to enhance the activity of the polymerases under storage and reaction conditions.

SUMMARY

In one aspect, a composition includes a polymerase in a buffer, where the polymerase is stabilized by a solubilized long-chain phospholipid in which the phospholipid comprises a tail with a carbon backbone of at least 8 carbons.

Various embodiments include one or more of the following features:

the solubilized long chain phospholipid is a phosphatidylcholine the composition includes a solubilizer such as an amphipathic molecule such as a lipid having a tail with a carbon backbone of no more than 8 carbons;

the polymerase is a thermostable polymerase;

the activity of the polymerase is greater in the presence of the solubilized phospholipid than in the absence of the solubilized phospholipid as can be measured in a replication assay by incorporation of deoxynucleoside triphosphate (dNTP).

The enhancement in polymerase activity in the presence of the solubilized phospholipid is at least 3-fold, for example at least 5-fold.

In a further aspect, a method includes stabilizing a polymerase in a buffer by adding a solubilized long-chain phospholipid in which the solubilized phospholipid has a tail with at least 8 carbons.

Various embodiments may include:

adding a solubilizer such as a lipid having one or more hydrophobic tails where the tail or tails have no more than 8 carbons forming the backbone of the tail; or obtaining an enhancement of the activity of the polymerase.

In a further aspect, a kit includes a polymerase in a buffer containing a solubilized phospholipid having at least one or more tails with a backbone of at least 8 carbons forming the tail and a stabilizer.

In a further aspect, a composition, is provided that includes a solubilized long-chain phospholipid in which the phospholipid has at least one hydrophobic tail containing at least 8 carbons

BRIEF DESCRIPTION OF THE DRAWINGS

FIGS. 1A-C, 2A-C, 3A-C, 4A-C, 5A-C, 6A-C, 7A-C and 8A-C described below show enhanced polymerase activity in a primer extension assay that was developed to measure the effect of solubilized long chain phospholipids on polymerase stability and activity. The embodiment of the assay uses: a serial dilution of Taq DNA polymerase (1.0-0.008 units per reaction in a 2-fold serial dilution); various percentage concentrations of specified solubilized long-chain phospholipids (0.3%, 0.1%, 0.025%, 0.005% and 0% detergent); M13 DNA; M13 primer; and labeled dNTPs. The results show an increase in dNTP-incorporation into a growing DNA polymer due to extension of the annealed M13 primer with time. These readings give a direct measure of polymerase activity.

The plots show that Taq DNA polymerase was substantially inactive as measured by dNTP-incorporation in the absence of the solubilized long-chain phospholipids. However, the stability and activity of Taq DNA polymerase was significantly improved when a long-chain phospholipid (having a hydrophobic tail of 8 carbons or greater) was used as a stabilizer, and a lipid (having a hydrophobic tail of 8 carbons or less) was used as a solvent. The greater the amount of long-chain phospholipid, the steeper the curve in the graph.

FIG. 1A shows the results using 1,2-dihexanoyl-sn-glycero-3-phosphocholine (diC$_6$PC) as a solubilizer and 1,2-dinonanoyl-sn-glycero-3-phosphocholine (diC$_9$PC) as a stabilizer.

FIGS. 1B and 1C shows the structure of the solubilizer and stabilizer respectively.

FIG. 2A shows the results of using diC$_6$PC as a solubilizer and 1,2-didecanoyl-sn-glycero-3-phosphocholine (diC$_{10}$PC) as a stabilizer.

FIGS. 2B and 2C shows the structure of the solubilizer and stabilizer respectively.

Figure 3:
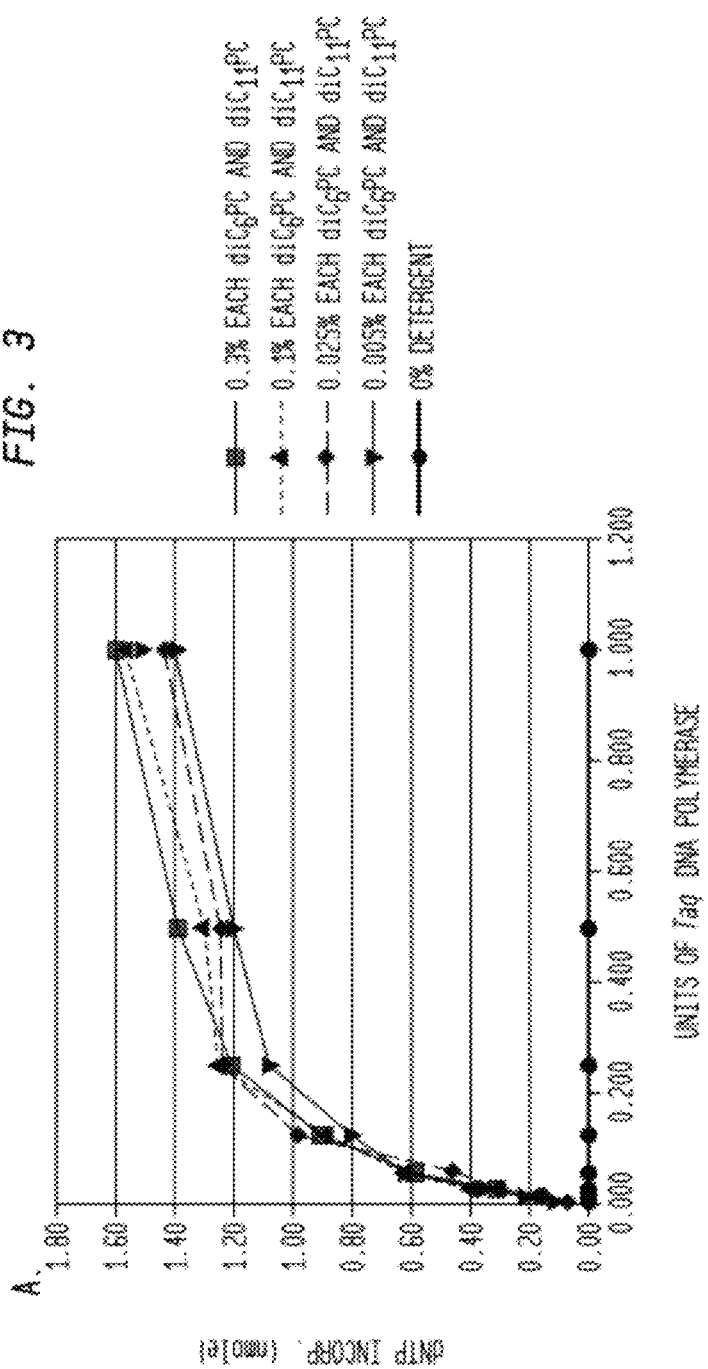

FIG. 3A shows the results of using diC$_6$PC as a solubilizer and 1,2-diundecanoyl-sn-glycero-3-phosphocholine (diC$_{11}$PC) as a stabilizer.

FIGS. 3B and 3C shows the structure of the solubilizer and stabilizer respectively.

FIG. 4A shows the results of using 1,2-diheptanoyl-sn-glycero-3-phosphocholine (diC$_7$PC) as a solubilizer and diC$_{10}$PC as a stabilizer.

FIGS. 4B and 4C shows the structure of the solubilizer and stabilizer respectively.

FIG. 5A shows the results of using 1,2-diheptanoyl-sn-glycero-3-phosphocholine (diC$_7$PC) as a solvent and an ether lipid 1,2-di-O-dodecyl-sn-glycero-3-phosphocholine (diOC$_{12}$PC) as a stabilizer.

FIGS. 5B and 5C shows the structure of the solubilizer and stabilizer respectively.

FIG. 6A shows the results of using a mono-substituted phosphatidylcholine 1-octanoyl-2-hydroxy-sn-glycero-3-phosphocholine (C$_8$PC) as a solubilizer and di-substituted phosphatidylcholine (diC$_{10}$PC) as a stabilizer.

FIGS. 6B and 6C shows the structure of the solubilizer and stabilizer respectively.

FIG. 7A shows the results of using a phosphorylcholine O-(octylphosphoryl)choline (OPC) as a solubilizer and a diC$_{10}$PC as a stabilizer.

FIGS. 7B and 7C shows the structure of the solubilizer and stabilizer respectively.

FIG. 8A shows the results of using a phosphorylcholine O-(decylphosphoryl)choline (DPC) as a solubilizer and a diC$_{10}$PC as a stabilizer.

FIGS. 8B and 8C shows the structure of the solubilizer and stabilizer respectively.

Figure 9:
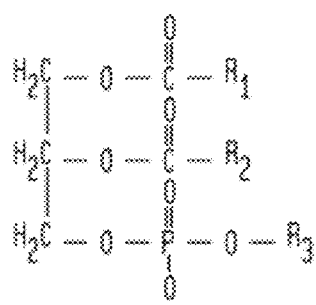

FIG. 9A shows a phospholipids core structure.

FIGS. 9B and 9C show $R_1$, $R_2$ and $R_3$ of the structure shown in FIG. 9A for stabilizers n≥8 and solubilizers n≤8. FIG. 9B shows $R_1$ and $R_2$ could be any of the following: —C$_n$H$_{2n+1}$, —C$_n$H$_{2n-1}$, —C$_n$H$_{2n-3}$, —C$_n$H$_{2n-5}$, —C$_n$H$_{2n-7}$, —C$_n$H$_{2n-9}$. FIG. 9C shows $R_3$ could be any of the following: —C$_5$H$_{13}$N, —H, —C$_2$H$_7$N, —C$_3$H$_7$O$_2$, —C$_3$H$_6$O$_2$ and —C$_6$H$_{11}$O$_5$.

Figure 10:
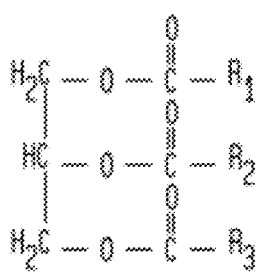

FIG. 10A shows a triglycerides core structure.

FIG. 10B shows $R_1$, $R_2$ and $R_3$, of the structure shown in FIG. 10A for stabilizers n≥4, could be any of the following: —C$_n$H$_{2n+1}$, —C$_n$H$_{2n-1}$, —C$_n$H$_{2n-3}$, —C$_n$H$_{2n-5}$, —C$_n$H$_{2n-7}$, —C$_n$H$_{2n-9}$.

Figure 11:
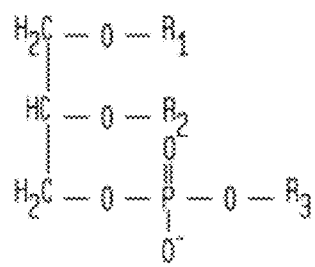

FIG. 11A shows an ether lipids core structure.

FIGS. 11B and 11C show $R_1$, $R_2$ and $R_3$ of the structure shown in FIG. 11A for stabilizers n≥8 and solubilizers n≤8.

FIG. 11B shows $R_1$ and $R_2$ could be any of the following: —C$_n$H$_{2n+1}$, —C$_n$H$_{2n-1}$, —C$_n$H$_{2n-3}$, —C$_n$H$_{2n-5}$, —C$_n$H$_{2n-7}$, —C$_n$H$_{2n-9}$.

FIG. 11C shows $R_3$ could be any of the following: —C$_5$H$_{13}$N, —H, —C$_2$H$_7$N, —C$_3$H$_7$O$_2$, —C$_3$H$_6$O$_2$ and —C$_6$H$_{11}$O$_5$.

Figure 12:
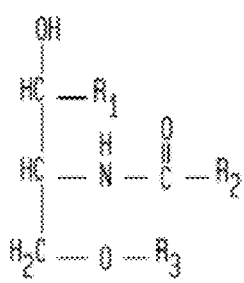

FIG. 12A shows a sphingolipids core structure.

FIGS. 12B and 12C show $R_1$, $R_2$ and $R_3$ of the structure shown in FIG. 12A for stabilizers n≥8 and solubilizers n≤8. FIG. 12B shows $R_1$ and $R_2$ could be any of the following: —C$_n$H$_{2n+1}$, —C$_n$H$_{2n-1}$, —C$_n$H$_{2n-3}$, —C$_n$H$_{2n-5}$, —C$_n$H$_{2n-7}$, —C$_n$H$_{2n-9}$. FIG. 12C shows $R_3$ could be any of the following: —PO$_3$C$_5$H$_{13}$N, —H, —PO$_3$C$_2$H$_7$N, —PO$_3$C$_3$H$_7$O$_2$, —PO$_3$C$_3$H$_6$O$_2$, —PO$_3$C$_6$H$_{11}$O$_5$, —P$_n$O$_{3n}$H, —C$_{6n}$H$_{10n+1}$O$_{5n}$, —C$_{6n}$H$_{10n}$O$_{5n}$, —C$_{6n}$H$_{10n-1}$O$_{5n}$, —C$_{6n}$H$_{10n-2}$O$_{5n}$, —C$_{6n}$H$_{10n-3}$O$_{5n}$, —C$_{6n}$H$_{10n+7n}$O$_{5n+3n}$N$_n$.

Figure 13:
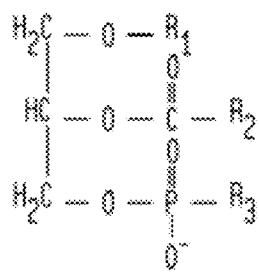

FIG. 13A shows a plasminogens core structure.

FIGS. 13B and 13C show $R_1$, $R_2$ and $R_3$ of the structure shown in FIG. 13A for stabilizers n≥8 and solubilizers n≤8. FIG. 13B shows $R_1$ and $R_2$ could be any of the following: —C$_n$H$_{2n+1}$, —C$_n$H$_{2n-1}$, —C$_n$H$_{2n-3}$, —C$_n$H$_{2n-5}$, —C$_n$H$_{2n-7}$, —C$_n$H$_{2n-9}$. FIG. 13C shows R3 could be any of the following: —C$_5$H$_{13}$N, —H, —C$_2$H$_7$N, —C$_3$H$_7$O$_2$, —C$_3$H$_6$O$_2$ and —C$_6$H$_{11}$O$_5$.

Figure 14:
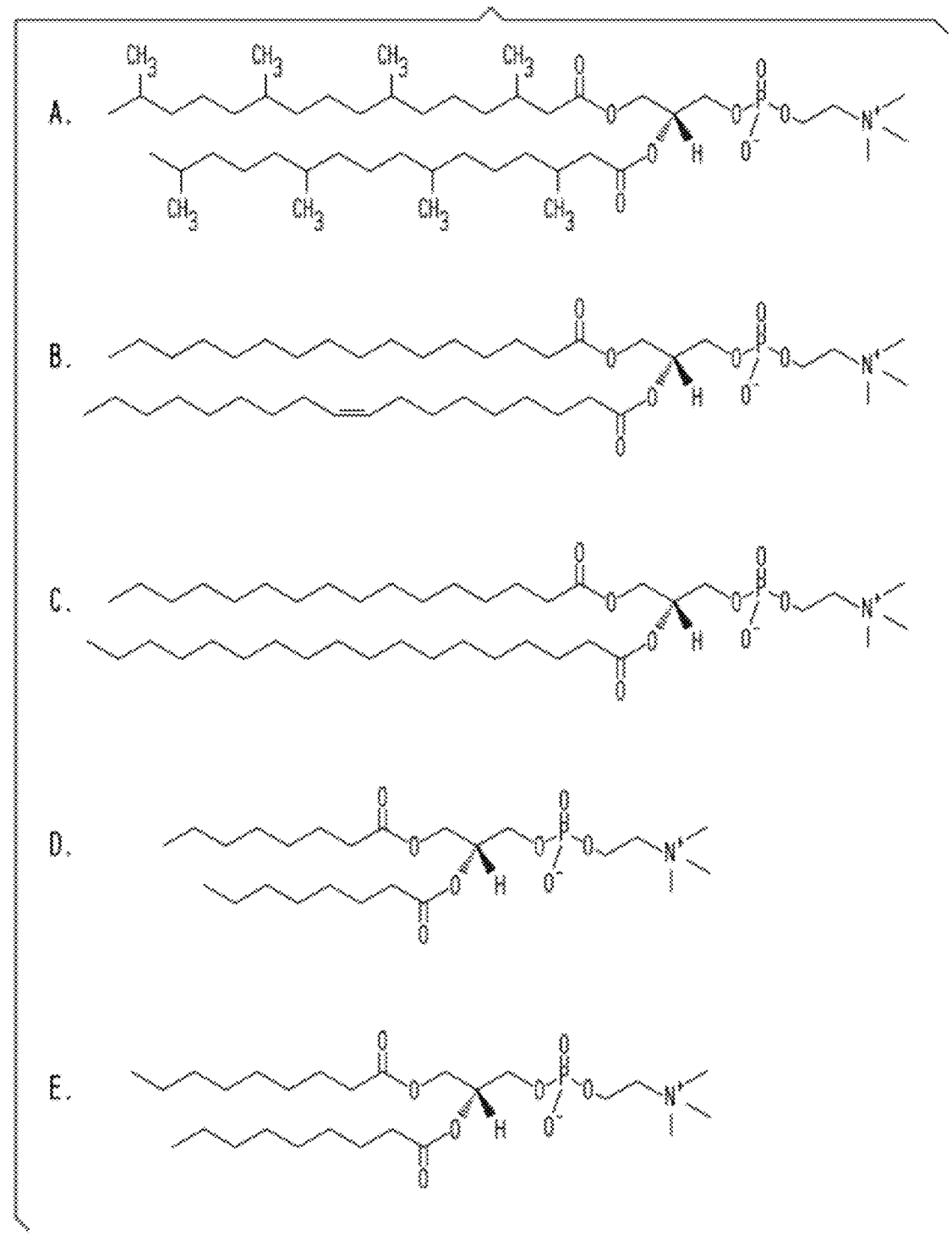

FIG. 14A shows the structure of 1,2 diphytanoyl-sn-glycero-3-phosphocholine suitable for use as a stabilizer.

FIG. 14B shows the structure of L-α-phosphatidylcholine suitable for use as a stabilizer.

FIG. 14C shows the structure of hydrogenated L-α-phosphatidylcholine suitable for use as a stabilizer.

FIG. 14D shows the structure of 1,2, dioctanoyl-sn-glycero-3-phosphocholine suitable for use as a solubilizer.

FIG. 14E shows the structure of 1,2-dinonanoyl-sn-glycero-3-phosphocholine suitable for use as a solubilizer.

DETAILED DESCRIPTION OF EMBODIMENTS

In embodiments of the invention, the problem of solubilization of a long chain phospholipid has been overcome making them suitable as stabilizers of polymerases in storage buffers and reaction buffers. The activity of solubilized long-chain phospholipids described herein was determined to reverse loss of activity as might occur during storage of the polymerase at −20° C. and also under reaction conditions as determined by measuring dNTP-incorporation.

Lack of solubility of the long-chain phospholipids that previously necessitated the formation of liposomes or vesicles (U.S. Pat. No. 5,792,612) was a deterrent for their use. This problem has been resolved here by adding one or more amphipathic molecules of an effective size to enable the long-chain phospholipid to remain in solution as a solubilizer of the otherwise insoluble long-chain phospholipid.

In all instances in which a solubilized phospholipid stabilizer has been tested, it has been found to perform efficiently and effectively for nucleic acid polymerase stability and activity.

A solubilized phospholipid stabilizer described herein is characterized by a hydrophilic head and at least one hydrophobic tail. It has been demonstrated that phospholipids having at least one tail with a carbon backbone of varying numbers of carbons preferably at least 8 carbons can act as stabilizers for nucleic acid polymerases although these molecules on their own are relatively insoluble in an aqueous buffer. According to the present embodiments, these molecules can be solubilized by adding one or more amphipathic molecules to the buffer.

Examples of stabilizers include phospholipids with at least one tail containing 8-30 carbons, e.g., 8-20 carbons, 8-16 carbons, or 8-12 carbons. These include the following: phosphatidylcholine, phosphatidylethanolamine, phosphatidic acid, phosphatidylglycerol, phosphatidylserine, and phosphatidylinositol; ether lipids such as 1,2-di-O-dodecyl-sn-glycero-3-phosphocholine; sphingolipids such as sphingosines, ceramides, sphingomyelin, gangliosides, glycosphingolipids, phosphosphingolipids, and phytosphingosine; and diacyl glycerols. Diacyl phospholipids with fatty acid chain lengths in the 8-30 carbon range tend to be insoluble without a suitable solubilizing agent. Additional examples of stabilizers having at least a 8 carbon chain include diC$_9$PC, diC$_{10}$PC, diC$_{11}$PC or diCO$_{12}$PC (FIGS. 1A-C, 2A-C and 3A-C) or diC$_{10}$PC. These are solubilized when combined with one or more amphipathic molecules exemplified by a lipid with no more than 8 carbons in the lipid carbon chain e.g., diC$_6$PC, diC$_7$PC, C$_8$PC, OPC and DPC (FIGS. 4A-B, 5A-B, 6A-B, 7A-B and 8A-B). Examples of core structures of stabilizers and solubilizers and examples of R groups are shown in FIGS. 9A-C, 10A-B, 11A-C, 12A-C and 13A-C.

Examples of solubilizing agents include amphipathic molecules such as lipids with one or two tails each containing 3-8 carbons. The lipid may optionally include one or more hydrophilic side chains. Examples of alternative solubilizing agents include phosphatidylcholine, phosphatidylethanolamine, phosphatidic acid, phosphatidylglycerol, phosphatidylserine, phosphatidylinositol; ether lipids such as 1,2-di-O-dodecyl-sn-glycero-3-phosphocholine; sphingolipids such as sphingosines, ceramides, sphingomyelin, gangliosides, glycosphingolipids, phosphosphingolipids, and phytosphingosine; and diacyl glycerols.

Additional solubilizing agents include anionic, cationic, zwitterionic, or non-ionic amphipathic molecules, for example, Triton® X-100 (Union Carbide Corp., Midland, Mich.), Tween®-20 (Uniqema Americas, LLC, Wilmington, Del.), IGEPAL® CA-630 (Rhodia Operations, Aubervilliers, France), Triton X-200 (obtainable from Sigma-Aldrich, St. Louis, Mo.), CHAPS, Octyl-β-glucoside, Octyl-α-glucoside, Decyl-β-D-maltoside, MEGA-8, ASB-C80, 3-(N,N-dimethyloctylammonio)propanesulfonate, Heptyl-β-D-1-thioglucoside, Sodium deoxycholate, Brij® 58 (Uniqema Americas LLC, Wilmington, Del., product obtained from Sigma-Aldrich, St. Louis, Mo.), 3-([3-Cholamidopropyl] dimethylammonio)-2-hydroxy-1-propanesulfonate (CHAPSO), 3-(4-Heptyl)phenyl-3-hydroxypropyl)dimethylammoniopropanesulfonate, Nonidet P-40 (obtained from Sigma-Aldrich, St. Louis, Mo.), Teepol 610 S (obtained from Sigma-Aldrich, St. Louis, Mo.), 3α,7β-Dihydroxy-5β-cholan-24-oic acid 5β-Cholan-24-oic acid-3α,7β-diol 7β-Hydroxylithocholic acid, Taurodeoxycholic acid sodium salt hydrate, Docusate sodium salt, N-Dodecanoyl-N-methylglycine, (Di-isobutylphenoxyethoxyethyl)dimethylbenzylammonium chloride, Pluronic® F-68 (BASF Corporation, Mount Olive, N.J., product obtained from Sigma-Aldrich, St. Louis, Mo.), N-Decyl-N,N-dimethyl-3-ammonio-1-propanesulfonate, Cocamidopropyl betaine, Lauramidopropyl betaine, Cholic Acid, Taurocholic Acid, Triton X-301 (Sigma-Aldrich, St. Louis, Mo.), Triton W-30 (Sigma-Aldrich, St. Louis, Mo.), Alkylether hydroxypropyl sultaine, Bis-(2-hydroxyethyl)isodecyloxypropylamine, and Cetylpyridinium chloride, Poly(ethylene glycol) 4-nonylphenyl 3-sulfopropyl ether potassium salt, Poly(ethylene glycol) monolaurate, Polyoxyethylene (150) dinonylphenyl ether and Nonyl nonoxynol-15 phosphate.

A single solubilizer or a plurality of solubilizers may be used together with a single stabilizer or a plurality of stabilizers in order to stabilize the polymerase in a storage buffer or as needed in a reaction buffer. A ratio of solubilizer to stabilizer may include 1:1 to 10:1 molar ratios with a concentration of solubilizer of 0.001% w/v to 0.5% w/v in the final enzyme reaction buffer. The effective ratio of solubilized stabilizer can readily be determined for different polymerases using the screening assays described in the examples below or other assays known in the art which measure polynucleotide amplification products.

Solubilized phospholipid have a stabilizing effect on a wide range of nucleic acid polymerases including DNA polymerases and thermostable nucleic acid polymerases. As used herein, "nucleic acid polymerase" or "polymerase" refers to an enzyme that catalyzes the polymerization of nucleotides. Generally, the enzyme will initiate synthesis at the 3'-end of the primer annealed to a nucleic acid template sequence, and will proceed in the 5'-direction along the template. "DNA polymerase" catalyzes the polymerization of deoxynucleotides. DNA polymerases and their properties are described in detail in, among other places, Kornberg, et al., DNA Replication, 2nd edition, W.H. Freeman, New York, N.Y. (1991) (Lundberg, et al., Gene, 108(1):1-6 (1991), provided by Stratagene, La Jolla, Calif., USA; Hinnisdaels, et al., Biotechniques 20:186-8 (1996); Myers and Gelfand, Biochemistry, 30:7661 (1991); Stenesh and McGowan, Biochimica et Biophysica Acta, 475:32 (1977); Diaz and Sabino, 1998. Brazilian Journal of Medical and Biological Research, 31:1239 (1998); Chien, et al., Journal of Bacteriology, 127:1550 (1976); Takagi, et al., 1997, Applied and Environmental Microbiology, 63:4504 (1997); International Publication No. WO 2001/32887; Lecomte and Doubleday, Nucleic Acids Research, 11:7505 (1983); Nordstrom, et al., Journal of Biological Chemistry, 256:3112 (1981); Cann, et al., Proc. Natl. Acad. Sci. USA, 95:14250-5 (1998)).

Examples of such DNA polymerases include bacterial polymerases such as: Taq DNA polymerase, Hemo KlenTaq® (Wayne M. Barnes, Chesterfield, Mo.) DNA polymerase, KlenTaq DNA polymerase, *Aquifex aeolicus* (Aae) DNA polymerase, *E. coli* DNA polymerase I, Klenow Fragment DNA polymerase, *Bacillus stearothermophilus* (Bst) DNA polymerase, large fragment, Bst DNA polymerase I, *Bacillus caldotenax* (Bca) DNA polymerase, Manta DNA polymerase, *Thermus thermophilus* (Tth) DNA polymerase, *Bacillus smithii* (Bsm) DNA polymerase, *Thermus brockianus* DNA polymerase; *Thermotoga maritima* (Tma) DNA polymerase; Archaeal DNA polymerases such as 9° N DNA polymerase such as Therminator™ (New England Biolabs, Inc., Ipswich, Mass.); Therminator gamma; Therminator II DNA polymerase, Therminator III DNA polymerase; Vent DNA polymerase (New England Biolabs, Inc., Ipswich, Mass.); Deep Vent™ DNA polymerase (New England Biolabs, Inc., Ipswich, Mass.); Pfu DNA polymerase; PfuCx DNA polymerase; Phusion® DNA polymerase (Finnzymes, now part of ThermoFisher Scientific, Waltham, Mass.); Phire® DNA polymerase (Finnzymes); Pwo DNA polymerase; KOD DNA polymerase; Neq DNA polymerase; *Sulfolobus* DNA polymerase IV; *Pyrococcus woesei* (Pwo) DNA polymerase (Roche Molecular Biochemicals, Indianapolis, Ind.), JDF-3 DNA polymerase (from *Thermococcus* sp. JDF-3; archaeal DP1/DP2 DNA polymerase II; viral polymerases such as T4 DNA polymerase; T7 DNA polymerase; Phi29 DNA polymerase; and reverse transcriptases such as Avian Myeloblastosis Virus (AMV) reverse transcriptase; Moloney Murine Leukemia Virus (MMLV) reverse transcriptase and Thermotogale reverse transcriptase.

Examples of mixtures of polymerase that may be stabilized include: Taq DNA polymerase and Deep Vent DNA polymerase; Taq DNA polymerase and Vent DNA polymerase; *Thermus brockianus* DNA polymerase and Deep Vent DNA polymerase; *Thermus brockianus* DNA polymerase and Vent DNA polymerase and Taq DNA polymerase and Vent (exo-) DNA polymerase; and Taq DNA polymerase and Phusion DNA polymerase.

Thermostable DNA polymerases that may be used in embodiments of the invention include, but are not necessarily limited to, the above recited polymerases and mutants, variants and derivatives thereof (see, for example, U.S. Pat. Nos. 5,436,149; 4,889,818; 5,079,352; 5,614,365; 5,374,553; 5,270,179; 5,047,342; and 5,512,462; International Publication Nos. WO 92/06188; WO 92/06200; and WO 96/10640; and Barnes, Gene, 112:29-35 (1992); Lawyer, et al., PCR Meth. Appl., 2:275-287 (1993); and Flaman, et al., Nucleic Acids Research, 22(15):3259-3260 (1994)).

DNA polymerases or mutants or variants thereof may be stabilized singly or in mixtures using the stabilizers described herein. These are exemplified below:

In one embodiment, the thermostable DNA polymerase is a Pfu DNA polymerase with a mutation at position V93, wherein the polymerase is exonuclease deficient (e.g. Deep Vent (exo⁻), Vent (exo⁻), Pfu V93 (exo⁻)). Methods of making and using Pfu V93 exo⁻ DNA polymerase are described in U.S. Publication No. US 2004-0091873. In another embodiment, the polymerase is a fusion protein having polymerase activity such as Pfu-Sso7 DNA polymerase, Vent-Sso7 DNA polymerase or Deep Vent-Sso7 DNA polymerase (U.S. Publication Nos.: 2007-0141591, 2005-0048530 and U.S. Pat. Nos. 7,666,645 and 7,541,170).

DNA polymerases may be stored in storage buffers either at 1× or at higher concentrations such as 10× for extended periods of time at room temperature or below room temperature. DNA polymerases may be introduced into a reaction mixture for purposes, for example, of amplification. These reaction mixtures may be used at high temperatures necessitated by the amplification protocol for variable but relatively short periods of time. The phospholipid stabilizer and solubilizer can be provided as a concentrated stock for use after dilution. For example, it may be provided at a 10× concentration in a 10× stock reaction buffer that is suitable for performing a nucleic acid amplification reaction. The 10× stock is diluted to a final 1× working concentration.

Examples of standard storage buffers for polymerases into which the present embodiments can be added contain 10 mM Tris-HCl, 100 mM KCl, 1 mM Dithiothreitol, 0.1 mM EDTA, and 50% Glycerol.

Examples of typical reaction buffers into which the present mix of solubilizer and stabilizer may be added include Taq standard buffer, Thermopol™ detergent-free buffers and detergent-free Phusion HF or GC buffer (New England Biolabs, Inc., Ipswich, Mass.). The reaction mixtures may include one or more of the following: primers, probes, labeled nucleotides and one or more reagents for labeling the DNA. DNA-labeling reagents include fluorophores, radiolabels and chemical moieties. DNA-labeling reagents may further include dual labels, Fluorescence Resonance Energy Transfer (FRET), the use of quenchers (see U.S. Publication No. 2008-0064071), and intercalating dyes or DNA binding dyes. The labeling reagents may be introduced into a storage buffer of a reaction mixture before its use or into the reaction buffer after the reaction (e.g., amplification) has occurred.

The solubilized phospholipid stabilizer of DNA polymerases can be used for any biological reaction in vitro for which DNA polymerases are used. Some of these applications are described in U.S. Publication No. 2008-0064071 and further include sequencing, cloning and DNA repair. A common use of DNA polymerases is in DNA amplification. Solubilized phospholipid stabilizers have been shown here to be effective at stabilizing a polymerase so as to enhance yields obtained during amplification. Examples of amplification reactions include thermocycling amplification reactions such as qPCR, PCR, RT-PCR, Direct PCR, PCR in the presence of inhibitors (e.g. hemoglobin, humic acid), Emulsion PCR and Bridge PCR; and isothermal amplification including loop-mediated isothermal amplification (LAMP), amplification such as bioluminescent assay in real time (BART)-LAMP and reverse transcriptase (RT)-LAMP; helicase-dependent amplification (HDA) including RT-HDA, strand-displacement amplification, rolling circle amplification, multiple-displacement amplification, recombinase polymerase amplification (RPA) and RT-RPA (Kim, et al., Bioanalysis 3(2):227-39 (2001); Gill, et al., Nucleic Acids Research, 27(3):224-43 (2008) as appropriate.

An embodiment of the invention includes a kit that comprises a package unit having one or more containers of the composition, and in some embodiments, includes containers of various reagents used for polynucleotide synthesis, including synthesis in PCR, sequencing, mutagenesis, and the like. Among other things, the kit may also contain one or more of the following items: polynucleotide precursors (e.g., nucleoside triphosphates), primers, probes, buffers, instructions, labeled nucleotides, intercalating dyes, and control reagents. The kit may include containers of reagents mixed together in suitable proportions for performing the methods in accordance with the invention. Reagent containers preferably contain reagents in unit quantities that obviate measuring steps when performing the subject methods. One exemplary kit according to embodiments also contains a DNA yield standard for the quantitation of the PCR product yields from a stained gel.

In one embodiment, the kit includes a master mix reagent comprising a thermostable polymerase, a phospholipid stabilizer/solubilizer, and polynucleotide precursors. In another embodiment, the kit includes a storage and/or reaction buffer having a polymerase and at least one phospholipid stabilizer/solubilizer. The storage buffer does not contain a detectable label in some configurations. A combination of two or more phospholipid stabilizers and one or more solubilizers may be provided. In yet another embodiment, the kits may further include a separate container having dNTPs. In another embodiment, any of the above kits may further include a separate container having a detectable label.

In an embodiment, the invention is directed to a kit which includes a purified polymerase, at least one phospholipid having a tail containing at least 8 carbons, an amphipathic solubilizer, polynucleotide precursors, and a labeled nucleotide. In yet another embodiment, the invention is directed to a kit which includes a purified polymerase, at least one phospholipid having greater than 8 carbons, an amphipathic solubilizer, polynucleotide precursors, and a DNA binding dye.

All references cited herein are incorporated in their entirety.

EXAMPLES

Enhancement of stability of a thermostable DNA polymerase (Taq) by the presence of stabilizer/solubilizer mixtures was investigated. Assays were developed for determining the reaction yield in primer extension assays, with or without the presence of phospholipids (obtained from Avanti Polar Lipids, Inc., Alabaster, Ala.), and amphipathic molecules (also from Avanti Polar Lipids, Inc.) after the polymerase was subjected to temperatures, which would be expected to inactivate the enzyme in the absence of non-ionic detergents.

Extension assays were performed in a 20-µl reaction mixture containing M13mp18 single-stranded DNA (6.7 nM) and a 20-fold excess of −47 sequencing primer (5'-CGC-CAGGGTTTTCCCAGTCACGAC-3') (SEQ ID NO:1). Assays also contained 10 mM Tris-HCl (pH 8.3), 50 mM KCl, 1.5 mM MgCl2, and 200 µM dNTPs. The Taq DNA polymerase was added to give the final concentrations shown in the figures. Taq DNA polymerase (800 U/µl) was stored in concentrated amounts in a detergent-free buffer (10 mM Tris-HCl (pH 7.4), 100 mM KCl, 1 mM dithiothreitol, 0.1 mM EDTA, and 50% glycerol). Prior to the assay, Taq DNA polymerase was diluted in storage buffer containing 3%, 1%, 0.025%, or 0.05% of each component of a lipid mixture. The enzyme was then added to the final reaction mixture in a 1/10 dilution. Standard reactions were also conducted in parallel in the absence of any lipids. Reactions were set up on ice, and then incubated in a thermal cycler (Applied Biosystems, now part of Life Technologies, Carlsbad, Calif.). Each reaction mixture, with or without lipids, was first heated at 94° C. for 2 minutes, then 72° C. for 10 minutes. The yield of reaction product was determined by including [3H]-dTTP (0.65 Ci/mmole, Perkin Elmer, Waltham, Mass.) in the reaction mixtures. Reaction products were spotted on DE81 filter disks (Whatman, part of GE Healthcare, Waukesha, Wis.) that were washed three times in 250 mM sodium acetate to remove unincorporated nucleotides. The radioactive incorporation on filters was determined by scintillation counting to calculate product yield.

The results are shown in FIGS. 1A-C, 2A-B, 3A-B, 4A-B, 5A-B, 6A-B, 7A-B and 8A-B. It was concluded that a lipid mixture stabilizes the polymerase and/or enhances polymerase activity if (a) the polymerase is stored in a buffer containing the lipid mixture at storage temperatures of typically −20° C., (b) the lipid mixture is added to the storage buffer at any time prior to the assay, and/or (c) the lipid mixture is added to the reaction mixture.

What is claimed is:

1. A composition comprising: a thermostable polymerase in a buffer comprising a solubilized long-chain phospholipid, wherein the phospholipid has at least one hydrophobic tail containing 8 to 30 carbons.

2. A composition according to claim 1, further comprising an amphipathic solubilizer.

3. A composition according to claim 2, wherein the amphipathic molecule is a lipid having a hydrophobic tail containing no more than 8 carbons.

4. A composition according to claim 1, wherein the at least one long-chain phospholipid is a phosphatidylcholine.

5. A composition according to claim 1, wherein the activity of the polymerase is enhanced in the presence of the solubilized phospholipid, capable of being measured in a replication assay by incorporation of deoxynucleoside triphosphate.

6. A composition according to claim 5, wherein the enhancement is at least 3-fold.

7. A kit, comprising:
a thermostable polymerase in a buffer containing a solubilized phospholipid having 8 to 30 carbons and a stabilizer.

8. A kit according to claim 7, wherein the stabilizer is a lipid having a hydrophobic tail containing no more than 8 carbons.

9. The composition of claim 1, wherein said thermostable polymerase is a Taq polymerase.

10. The composition of claim 1, wherein the phospholipid has at least one hydrophobic tail containing 8 to 20 carbons.

* * * * *